(12) United States Patent  
Pologe

(10) Patent No.: US 6,560,470 B1  
(45) Date of Patent: May 6, 2003

(54) ELECTRICAL LOCKOUT PHOTOPLETHYSMOGRAPHIC MEASUREMENT SYSTEM

(75) Inventor: Jonas A. Pologe, Boulder, CO (US)

(73) Assignee: Datex-Ohmeda, Inc., Madison, WI (US)

( * ) Notice: Subject to any disclaimer, the term of this patent is extended or adjusted under 35 U.S.C. 154(b) by 121 days.

(21) Appl. No.: 09/712,863

(22) Filed: Nov. 15, 2000

(51) Int. Cl.[7] ............................. A61B 5/00; A61B 18/04
(52) U.S. Cl. .......................... 600/310; 600/323; 606/32
(58) Field of Search ........................... 600/310, 323, 600/342; 606/32, 41, 42

(56) References Cited

U.S. PATENT DOCUMENTS

| | | | |
|---|---|---|---|
| 3,894,532 A | * 7/1975 | Morey .................. | 128/907 |
| 4,441,027 A | * 4/1984 | Richardson et al. ... | 128/200.13 |
| 4,776,339 A | * 10/1988 | Schreiber .................. | 600/324 |
| 4,846,183 A | 7/1989 | Martin .................. | 128/633 |
| RE33,643 E | 7/1991 | Isaacson et al. .......... | 128/633 |
| 5,099,123 A | 3/1992 | Harjunmaa .............. | 250/345 |
| 5,193,543 A | 3/1993 | Yelderman .............. | 128/633 |
| 5,282,466 A | * 2/1994 | Duffy et al. .............. | 600/323 |
| 5,341,804 A | 8/1994 | Fogt et al. .............. | 128/633 |
| 5,429,128 A | 7/1995 | Cadell et al. ............ | 128/633 |
| 5,582,169 A | 12/1996 | Oda et al. ................ | 128/633 |
| 6,387,092 B1 | * 5/2002 | Burnside et al. .......... | 606/32 |

* cited by examiner

*Primary Examiner*—William C. Doerrler  
(74) *Attorney, Agent, or Firm*—Marsh Fischmann & Breyfogle LLP

(57) ABSTRACT

A photoplethysmographic measurement system includes an electrical lockout to effectively prevent users, such as patients and medical personnel, from being exposed to high levels of light energy illuminating from light emitters (18) housed within a main instrument (10) when a probe (12) becomes detached from the system during use. The probe (12) is provided with a resistor having a range of resistor values. In use, the electrical lockout frequently or continuously interrogates the probe connection and determines whether the detected value of the resistor falls within predetermined allowable levels. If the probe (12) inadvertently becomes disconnected from the main instrument, the value of the resistor will fall outside of the predetermined allowable levels indicative of an incompatible probe, an improper coupling of the probe, or a complete detachment of the probe. In this case, lockout switch (44) is employed to inhibit activation of the light emitters (18). When a proper connection is re-established, the electrical lockout will recognize the value of the detected resistor and send a signal to close the lockout switch (44), allowing current to pass and re-energize the light sources. Alternatively or in addition, the electrical lockout may include a circuit or a mechanism for detecting a presence of a light sensor (34) in the probe by checking for the appropriate forward voltage drop on the conductors (38) connected to the light sensor.

23 Claims, 2 Drawing Sheets

ELECTRICAL LOCKOUT PHOTOPLETHYSMOGRAPHIC MEASUREMENT SYSTEM

FIELD OF THE INVENTION

The present invention generally relates to photoplethysmographic measurement systems and, in particular, to an electrical lockout for avoiding undesired transmission of optical signals by such photoplethysmographic measurement systems.

BACKGROUND OF THE INVENTION

In the field of photoplethysmography, light pulses from different portions of the electromagnetic spectrum are used to noninvasively measure various blood analytes or blood oxygen saturation in a test subject. The photoplethysmography measurement system generally includes a main instrument, a removable probe for attaching to a patient during a test, and a signal transmitter for delivering signals between the main instrument and the probe. Because the probe ordinarily makes direct contact with the patient's body during a medical examination, it is desirable that probes be disposable in order to reduce the risk of infection. Accordingly, the probe is typically detachable from the main instrument via a coupling disposed somewhere between the probe and housing.

To reduce cost and to make the removable probe head affordable as a disposable unit, the componentry of the probe head is minimized by separating the light sources from the probe head to the main instrument or to another portion of the system (such as within a connector extending from the housing to the probe) that is detachably coupled to the probe head. While such disposable probe heads are relatively inexpensive to manufacture since the expensive light source elements and processing circuitry are located in the main instrument, the presently known photoplethysmography measurement devices do pose certain shortcomings. The light output from the fiber optic cable in conventional systems typically remains continuously turned on as long as the main instrument remains turned on. Thus, when the probe head becomes detached while the main instrument is active, the intense light emission from the end of the fiber optic cable could potentially expose a patient or clinician to intense illumination.

SUMMARY OF THE INVENTION

The inventor has recognized that the operation of a photoplethysmographic measurement system may be further enhanced by incorporating a safety feature to effectively prevent users, such as patients and medical personnel, from being exposed to high levels of light energy from the system when a probe becomes detached from the system during use. If the main instrument is able to sense when the probe becomes detached therefrom, certain operations may be performed therein in order to avoid energizing, or to de-energize, the light sources upon receiving an indication that the probe detached therefrom.

According to one aspect of the invention, any appropriate means for sensing detachment of the probe from the main instrument may be used. The present invention may employ inherent features of the probe and the coupling device in order to detect detachment of the probe. The coupling device between the main instrument and probe generally includes optical and electrical connections. For purposes of sensing detachment, the main instrument may be configured to detect breach of either the optical or the electrical connection. Alternatively, new features may be added to the system for purposes of providing feedback. For example, a resistor or other electrical component may be incorporated into the probe so as to provide an electronic signature or a feedback. In this case, the main instrument has a feedback detector for detecting such an electrical component in the probe when it is properly connected thereto. Furthermore, the present invention may use a dedicated sensor in order to provide indication of proper connection. For example, the connector port may be provided with a contact for purposes of indicating connection with the probe. Alternatively, an optical sensor may be employed to provide indication of connection across coupling sections.

According to the invention, a photoplethysmographic measurement system for noninvasively measuring various blood analytes in a patient's appendage is provided. The measurement system includes an electrical lockout which frequently or continuously interrogates the probe connection and automatically disconnects current flow to the light emitters upon receiving an indication that the probe or the cable is detached. The probe may include one or more preselected electrical elements which can be detected by the lockout of the main instrument. For purposes of determining if the probe is properly connected or has been accidentally disconnected, the electrical lockout frequently or continuously monitors an absence or presence of such electrical element.

In one embodiment, the probe is provided with a resistor having a predetermined resistor value. In use, the electrical lockout continuously interrogates the probe connection in order to determine whether the value of the detected resistor falls within predetermined allowable levels. If the probe accidentally becomes disconnected from the main instrument, the detected value of the resistor will fall outside of the predetermined allowable levels indicative of an incompatible probe, an improper coupling of the probe, or a complete detachment of the probe. In this case, the lockout switch is employed to inhibit activation of the light emitters. When a proper connection is re-established, the electrical lockout will recognize the value of the detected resistor and send a signal to close the lockout switch, allowing current to pass and re-energize the light sources.

In this embodiment, the value of the resistor also serves to identify the type of probe presently connected to the system. A probe may be uniquely designed for attaching to a given appendage of a patient, such as a finger, earlobe, or the nasal septum so as to accommodate a variety of monitoring, conditions and situations. For purposes of obtaining the most accurate measurement, the identified probe-type information may be employed to determine the appropriate input light signals to be used to illuminate the patient's appendage and the appropriate computation to be used to process the transmitted light signals.

In another embodiment, the electrical lockout may include means for detecting the presence of a light sensor in the probe by checking for the appropriate forward voltage drop on the conductors connected to the light sensor.

In another embodiment, the probe is provided with a bandgap reference, wherein the amplitude of the bandgap reference voltage generated within the probe will be used to determine the presence and identify the type of probe. In this case, the electrical lockout includes a voltage detector to interrogate for a voltage drop at certain allowable levels at the probe head. If the bandgap reference voltage falls outside of the predetermined allowable voltage levels, the lockout will send a signal to open a lockout switch to turn off the light emitters.

In yet another embodiment, a contact, or set of contacts in the probe are required to continue to power the light emitters. Thus disconnecting the probe removes power (or turns off a control signal) to the light emitters thus turning off the light emitters.

Finally, any of these techniques may be used in combination to eliminate the possibility of emitters staying on in the presence of a single point failure.

DETAILED DESCRIPTION OF THE PREFERRED EMBODIMENTS

Figure 1:
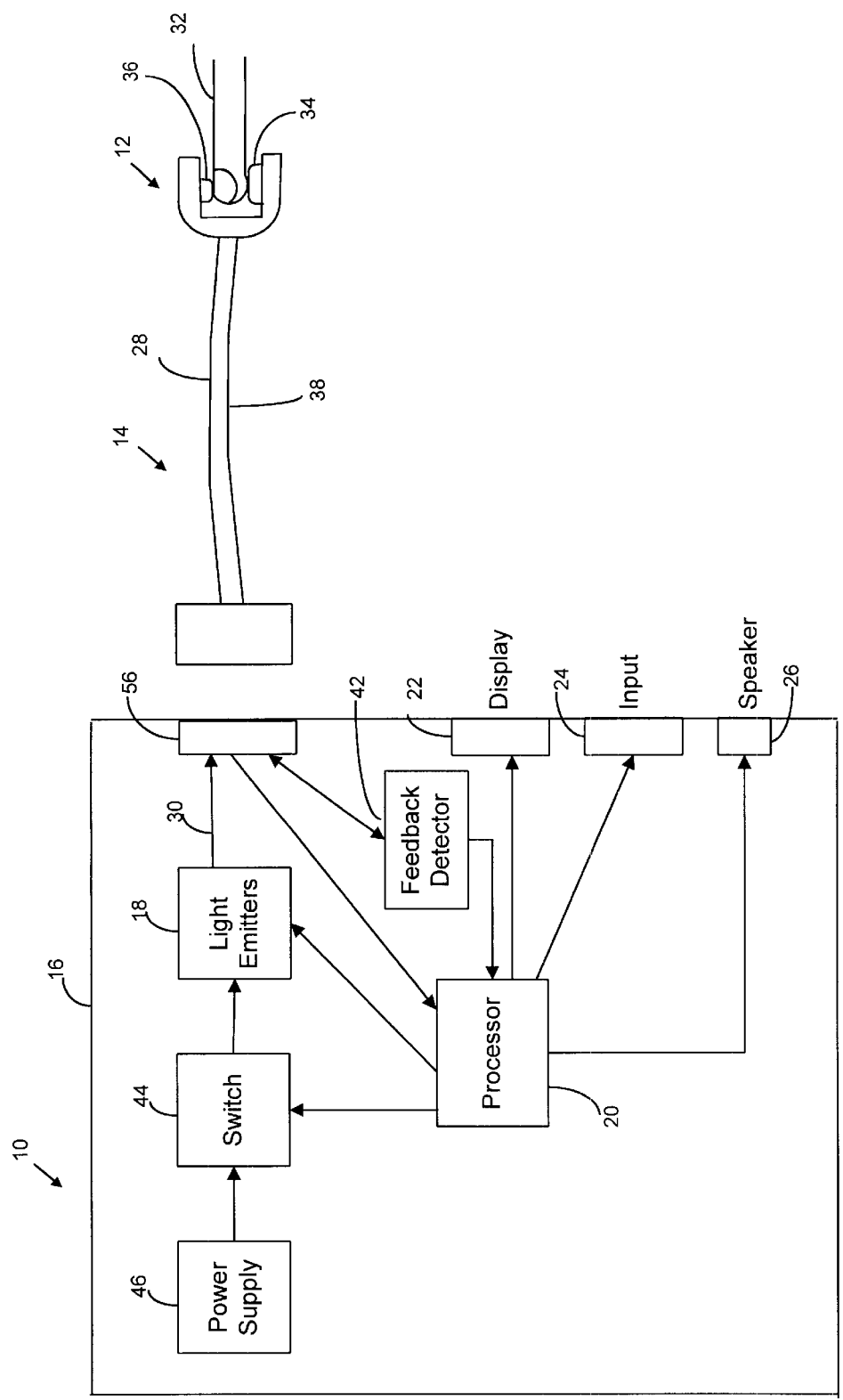
FIG. 1 is a block diagram illustrating an electrical lockout for a photoplethysmographic measurement system in accordance with a preferred embodiment of the present invention.

Referring to FIG. 1, an electrical lockout photoplethysmographic measurement system according to the present invention is shown. The photoplethysmographic measurement system is used to noninvasively measure various blood analytes in a tissue of a patient. For example, the photoplethysmographic measurement system may be a pulse oximetry system which noninvasively measures the oxygen saturation level. In the illustrated embodiment, the electrical lockout photoplethysmographic measurement system is a pulse oximeter generally including a main instrument 10, a probe 12, and a signal transmission cable 14 connected between the main instrument and the probe head.

The main instrument 10 includes a housing 16 which contains a plurality of light emitters 18 such as light emitting diodes (LED) or laser diodes, each emitter generating a light signal at a predetermined wavelength. The main instrument 10 also includes a processor 20 which provides all the computation capability necessary to control the overall operation of the system, and a display unit 22 for displaying measurement information regarding the patient to the physician. In addition, to enable a user to input various monitoring parameters, an input device 24 such as control knobs and/or a keypad is provided. A speaker 26 is connected to the processor 20 to audibly alert the user of potentially dangerous analyte levels.

The signal transmission cable 14 includes one or more optical light guides 28, such as a fiber optic cable for delivering optical signals between the probe and the main instrument 10. The signal transmission cable 14 may be fixedly connected to the probe 12 as a single unit. Alternatively, the probe may be detachably connectable to the cable. In a preferred embodiment as illustrated in FIG. 1, the signal transmission cable 14 is configured so that it is detachably connectable at both probe 12 and the main instrument 10. The light signals 30 generated by the light sources 18 are transmitted via the signal transmission cable and are directed onto an appendage 32 of the patient via the probe.

The probe 32 includes an attachment mechanism for securely attaching to a patient's appendage, such as a finger, earlobe, or the nasal septum, during a medical examination. For example, the probe body may include a spring-loaded hinge for clamping on a patient's finger or velcro for securely wrapping the probe on an appendage. The probe also includes a light direction guide 36 to allow the light signal generated by the emitters to be directed substantially perpendicular to the surface of the skin and the blood carried thereunder. In this regard, the guide 36 may include a mechanism for aligning the fiber end or a mirror associated with the fiber terminal. The light signals transmitted through the appendage may be delivered back to the main instrument optically; for example, via a second fiber optic cable in the signal transmission cable. Alternatively and as illustrated in FIG. 1, the transmitted light signals are delivered electrically for processing by the processor. In this embodiment, a light sensor 34 is provided on the probe located on the other side of the light direction guide 36 for receiving the light signals transmitted through the patient's appendage and converting the received light signals into electrical output signals. In this case, an electrical conductor 38 is connected to the light sensor 34 in the probe to deliver the electrical output signals to the processor 20.

To perform measurement of the oxygen saturation level, the probe 12 is first attached to the patient's appendage 32, the light signals carried by the fiber optic cable 28 illuminates the appendage, and after the intensity of the light signal has been affected by the blood in the appendage, the light sensor 34 is used to convert the transmitted light signals into an electrical output signal. The electrical output signal produced by the light sensor has characteristics that are a function of the blood oxygen saturation level. The processor 20 in the main instrument receives the electrical output signals from the light sensor and processes them to determine the patient's blood oxygen saturation level. The results of the measurement computations are then displayed on the display 22. The computation methods to determine the blood analyte level in the arterial blood are well-known to those skilled in the art, and are not discussed herein.

In accordance with the present invention, an electrical lockout is provided to prevent the light emitters 18 from transmitting high intensity light beams when the probe is detached from the main instrument. The probe 12 may include one or more preselected electrical elements which can be detected by the main instrument 10. For purposes of determining whether the probe is connected or disconnected, the electrical lockout of the present invention is designed to continuously monitor an absence or presence of such electrical element(s).

In a preferred embodiment, the preselected electrical element is a resistor having a predetermined resistor value. The resistor serves a dual purpose. First, the resistor facilitates in determining whether the probe 12 is properly connected. Second, the resistor facilitates in identifying the type of probe. The electrical lockout will continuously interrogate the probe connection and determine whether the detected resistor value falls within predetermined allowable levels. If the detected resistor value falls within the predetermined allowable levels, the value of the resistor is used to identify the type of probe presently being used. The probe may be manufactured in various types, each being configured for attaching to a specific part of a patient's body, such as a finger, earlobe, or the nasal septum so as to accommodate variations in size and shape of the patient's appendage. Further, the resistor value may also be used to identify the manufacturer of the probe as well as to identify the type of probe.

The electrical lockout includes a lockout switch 44 connected serially between the power supply 46 and the light emitters 18 and a feedback detector 42 such as a resistor detector connected to connector port 56 for detecting the value of the resistor in the probe. Although illustrated as a separate component for purposes of illustration, it will be appreciated that the detector 42 may be embodied as a software executed by processor 20 or other logic module. It will also be appreciated that the lockout switch 44 may be incorporated into the light emitters 18 as a single integral unit. The processor 20 includes an input connected to the output of the resistor detector 42. The processor is connected to the lockout switch and provides switch disable and switch enable signals to control the lockout switch. When proper connection is established, the lockout switch remains closed to permit current flow until receiving a switch disable signal from the processor. In the event that an unrecognizable resistor value is detected by the resistor detector, the switch disable signal is provided by the processor to open the lockout switch. It will be appreciated that a detached probe would be perceived at the processor 20 as an open circuit corresponding to an unrecognizable resistor value. It should also be noted that the lockout circuit prevents use of the emitters 18 with an incompatible system having no recognizable resistor value.

Figure 2:
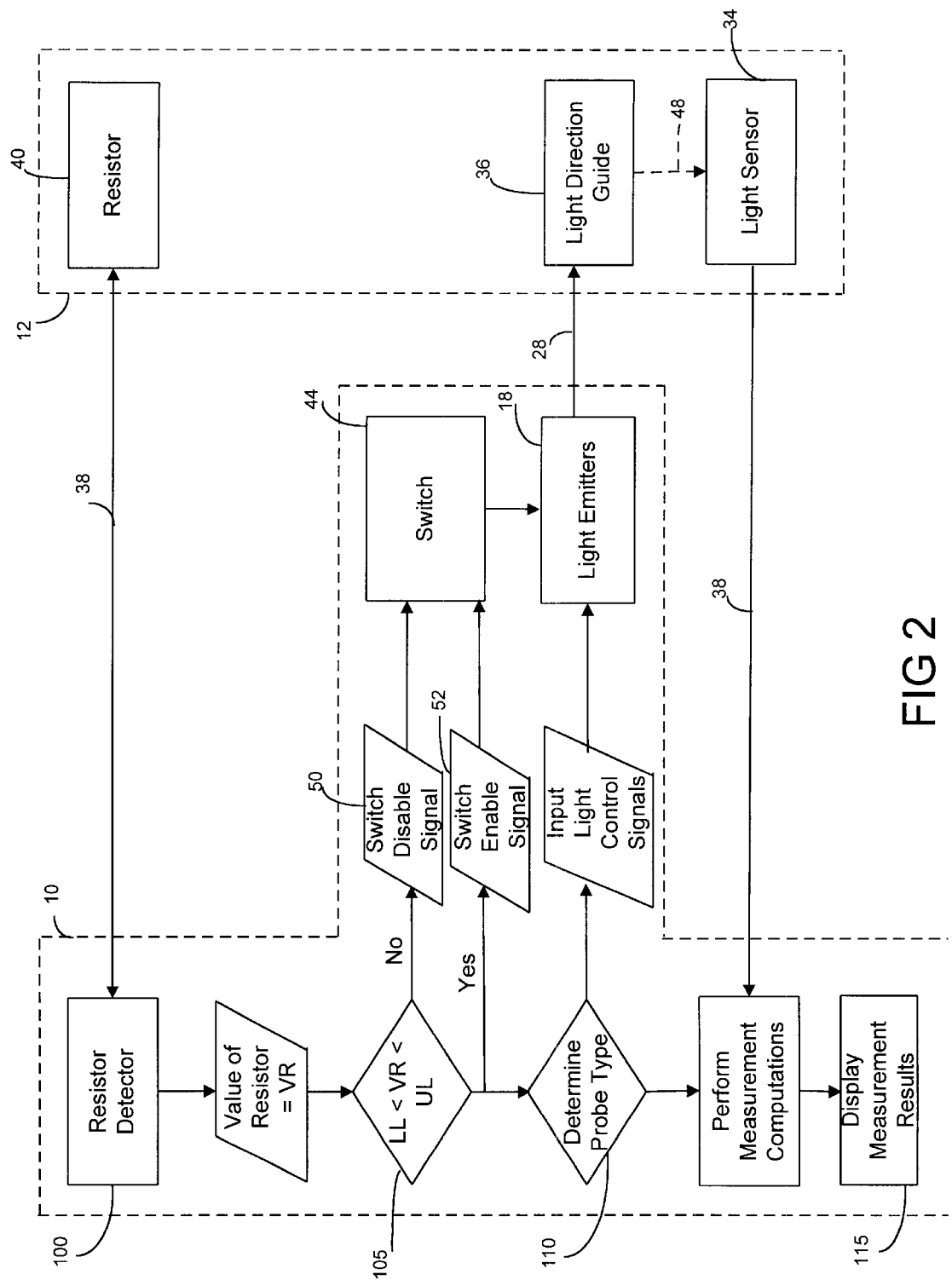
FIG. 2 is a flowchart diagram illustrating the operation of the photoplethysmographic measurement system of the invention.

Referring now to FIG. 2, a flowchart diagram illustrating operation of the processor and the electrical lockout in the photoplethysmographic measurement system is shown. In step 100, the resistor detector 42 continuously interrogates the resistor 40 located in the probe 12 to detect the value of the resistor (VR). In step 105, the processor receives this VR and determines if it is within predetermined allowable levels. If it is, this indicates that the probe head is properly coupled to the main instrument. In this case and as shown in step 110, the processor determines the type of probe connected to the main instrument based on the value of the resistor received from the resistor detector. For purposes of obtaining the most accurate measurement, the identified probe type information may be employed to determine the appropriate input light signal to be used to illuminate the patient's appendage and the appropriate computation to be used to process the return signal.

In addition, the processor sends a switch enable signal 52 to the switch 44 to provide a closed circuit between the power supply 46 and the light emitters 18. The light emitters 18 remain turned on, and the light signals generated therefrom are transmitted via the optical light guide 28 to the probe 12. The light signals are then directed by the light direction guide 36 into the tissue under examination, such as a finger or an earlobe, travel through the tissue, and emerge on the other side of the tissue. The transmitted light signals 48 are received by the light sensor 34 and delivered back to the main instrument 10 via the electrical conductor 38. The processor unit processes the electrical output signals delivered from the light sensor to determine various blood analyte related values, such as the oxygen saturation level, in the tissue. In step 115, the results of the measurement computations are then displayed on the display.

If the detected resistor value falls outside of the predetermined range, this indicates that the probe is not properly connected to the main instrument, or that an incompatible probe is connected. In this case, a switch disable signal 50 is provided by the processor to open the lockout switch 44 in order to turn off its light sources 18. When a proper connection is re-established, the processor will recognize the value of the resistor detected by the detector and send a switch enable signal to close the lockout switch, allowing current to pass and re-energize the light sources.

Alternatively or in addition, the main instrument includes a circuit or a mechanism for detecting a presence of the light sensor in the probe by checking for the appropriate forward voltage drop on the electrical conductors connected to the light sensor. In this embodiment, the feedback detector 42 may be a voltage detector used to sense a voltage drop at the probe head. In the event that such interrogations indicate that the probe is not present or is otherwise not prepared for proper functioning, the lockout is employed to inhibit activation of the light sources.

In yet another alternative embodiment of the present invention, the family identifier (resistor) may be replaced by the presence or absence of a bandgap reference. The amplitude of the bandgap reference voltage generated within the probe will be used to determine the presence and type of probe. The main instrument will interrogate for a voltage drop at certain allowable levels at the probe head. In this case, the detector 42 may be a voltage detector used to sense a voltage drop at the probe head. If the bandgap reference voltage is below or above the predetermined allowable voltage levels, the processor will send to a switch disenable signal to the lockout switch.

In its most rudimentary form, in one embodiment of the current invention, one or more contacts of the probe connector are used to provide continuity of electrical power (or of a light emitter enable signal to the switch 44) to the light emitters circuitry.

While the foregoing preferred embodiments of the invention have been described and shown, it is understood that variations and modifications, such as those suggested and others within the spirit and scope of the invention, may occur to those skilled in the art to which the invention pertains. The scope of the present invention accordingly is to be defined as set forth in the appended claims.

What is claimed is:

1. A lockout apparatus for a photoplethysmographic instrument comprising:
    a main instrument having an illumination source for generating a light signal;
    a probe for directing said light signal;
    a signal transmission assembly for delivering said light signal generated by said illumination source to said probe;
    said signal transmission assembly including a first transmission portion, a second transmission portion, and a connector for detachably connecting said first and second portions; and
    lockout means for inhibiting transmission of said light signal across said connector when said probe is detached from said main instrument.

2. The system as claimed in claim 1 wherein said lockout means comprises means for preventing said illumination source from transmitting said light signal when said probe is detached from said main instrument.

3. The system as claimed in claim 2, wherein said probe is configured for attachment to an appendage of said test subject and for directing said light signal thereto.

4. The system as claimed in claim 1, wherein:
    said lockout means comprises means for determining if said probe is properly coupled to said main instrument via the signal transmission assembly, and means for disabling said illumination source when said probe is detached from said main instrument.

5. The system as claimed in claim 1, wherein:
    said probe includes at least one electrical element; and
    said lockout means includes means for detecting an absence or presence of said at least one electrical element.

6. The system as claimed in claim 5, wherein said electrical element is a resistor having a predetermined value, said predetermined value of the resistor corresponding to a specific type of probe.

7. The system as claimed in claim 6, wherein said lockout means comprises a resistor detector for detecting a resistive value of said resistor of said probe and a switch connected to said illumination source for disabling said illumination source based on said detected resistive value.

8. The system as claimed in claim 5, wherein said electrical element provides a band gap reference having a predetermined amplitude, said predetermined amplitude of said band gap reference corresponding to a specific type of probe.

9. The system as claimed in claim 1, wherein said illumination source comprises a plurality of light emitters, said plurality of light emitters including one of a light emitting diode (LED) or a laser diode.

10. The system as claimed in claim 1, wherein said signal transmission assembly includes a fiber optic assembly for delivering optical signals between the probe and the main instrument.

11. The system as claimed in claim 10, wherein said fiber optic assembly is fixedly connected to said probe as a single unit.

12. The system as claimed in claim 10, wherein said probe is detachably connected to the fiber optic cable.

13. A photoplethysmographic measurement system for noninvasively measuring a value related to at least one blood analyte in a tissue of a test subject, comprising:

a main instrument having an illumination source for generating a light signal;

a probe for directing said light signal onto the tissue;

an electro-optical cable detachably connectable between said main instrument and said probe for delivering said light signal generated by said illumination source to said probe; and lockout means for making a determination as to whether said probe is properly coupled to said main instrument via the cable, and for selectively disabling said illumination source based on said determination.

14. The system as claimed in claim 13, wherein:

said probe includes at least one electrical element; and said lockout means includes means for detecting said at least one electrical element.

15. The system as claimed in claim 14, wherein said electrical element is a resistor having a predetermined value, said predetermined value of the resistor corresponding to a specific type of probe.

16. The system as claimed in claim 14, wherein said electrical element provides a bandgap reference having a predetermined amplitude, said predetermined amplitude of said bandgap reference corresponding to a specific type of probe.

17. The system as claimed in claim 15, wherein said lockout means is a lockout circuit located within said main instrument.

18. The system as claimed in claim 17, wherein said lockout circuit comprises a resistor detector for detecting a resistive value of said resistor of said probe and a switch connected to said illumination source for disabling said illumination source when said value of the resistor is above or below predetermined allowable levels.

19. A method for preventing users from being exposed to high levels of light energy illuminating from a photoplethysmographic system having a main instrument with at least one illumination source for generating a light signal, a probe head, and an electro-optical cable detachably connected between the main instrument and the probe head for carrying said light to the probe head, said method comprising:

determining if said probe head is coupled to said main instrument; and disabling said illumination source when said probe head is detached from said main instrument.

20. The method as claimed in claim 19, wherein:

said probe head includes at least one electrical element; and said determining step includes using said main instrument to perform an interrogation to detect an absence or presence of said at least one electrical element.

21. The method as claimed in claim 20, wherein said electrical element is a resistor having a predetermined value, and said step of determining comprises detecting an absence or presence of said electrical element having said predetermined value.

22. The method as claimed in claim 20, wherein said electrical element provides a bandgap reference having a predetermined amplitude, and said step of determining comprises detecting a presence or absence of said bandgap reference having said predetermined amplitude.

23. A lockout apparatus for a photoplethysmographic system comprising:

a main instrument having an illumination source for generating a light signal;

a probe for directing said light signal;

a signal transmission assembly for delivering said light signal generated by said illumination source to said probe;

said signal transmission assembly including a first transmission portion, a second transmission portion, and a connector for detachably connecting said first and second portions; and lockout means disabling the system when said probe is detached from said main instrument;

said lockout means comprising means for determining if said probe is properly coupled to said main instrument via the signal transmission assembly, and means for disabling said system when said probe is detached from said main instrument, wherein said electrical element provides a band gap reference having a predetermined amplitude, said predetermined amplitude of said band gap reference corresponding to a specific type of probe.

* * * * *